United States Patent [19]

Ueno et al.

[11] 4,229,570
[45] Oct. 21, 1980

[54] METHOD OF PRODUCING NITROGEN-CONTAINING POLYSACCHARIDES

[75] Inventors: Saburo Ueno, Tokyo; Chikao Yoshikumi, Kunitachi; Fumio Hirose, Tokyo; Yoshio Omura, Tanashi; Toshihiko Wada, Mibu; Takayoshi Fujii, Tokyo; Eiichi Takahashi, Kawaguchi, all of Japan

[73] Assignee: Kureha Kagaku Kogyo Kabushiki Kaisha, Tokyo, Japan

[21] Appl. No.: 788,991

[22] Filed: Apr. 19, 1977

[30] Foreign Application Priority Data

Jul. 7, 1976 [JP] Japan .................................. 51-80665

[51] Int. Cl.$^2$ ......................... A61K 31/73; C07H 1/08
[52] U.S. Cl. ........................................... 536/18; 536/1
[58] Field of Search ........................................... 536/1

[56] References Cited

U.S. PATENT DOCUMENTS

| | | | |
|---|---|---|---|
| 3,382,229 | 5/1968 | Patton et al. | 536/1 |
| 3,436,311 | 4/1969 | Ferguson et al. | 536/1 |
| 3,759,896 | 9/1973 | Komatsu et al. | 536/1 |
| 3,933,788 | 1/1976 | Kang et al. | 536/1 |
| 4,051,314 | 9/1977 | Ohtsuka et al. | 536/1 |

*Primary Examiner*—Johnnie R. Brown
*Attorney, Agent, or Firm*—Stevens, Davis, Miller & Mosher

[57] ABSTRACT

The fungi belonging to the Coriolus genus is first extracted with water or a dilute alkaline solution and then further extracted stepwise by using alkaline solutions with gradually increased concentrations to obtain a nitrogen-containing polysaccharide having an antitumor activity in a high yield.

4 Claims, No Drawings

METHOD OF PRODUCING NITROGEN-CONTAINING POLYSACCHARIDES

FIELD OF THE INVENTION

This invention relates to a method of advantageously producing a nitrogen-containing polysaccharide having an anti-tumour activity by extracting a fungus of the class Basidiomycetes belonging to the Coriolus genus in multiple stages by using an aqueous solvent.

BACKGROUND OF THE INVENTION

It is known that a polysaccharide having an anti-tumour activity can be obtained by refining the extract of a Basidiomycetes with an aqueous solvent. Such method, however, has a serious drawback that the extraction efficiency of the active component is low, resulting in sizable loss of the valuable anti-tumour substance, and hence such method has little practical utility, particularly from the viewpoint of adaptability to industrial production of an anti-tumour substance from the fungus.

BRIEF SUMMARY OF THE INVENTION

We have found that a nitrogen-containing polysaccharide having an anti-tumour effect and other various pharmacodynamic effects can be obtained in a high yield when a fungus belonging to the Coriolus of Polyporaceae of the class Basidiomycetes is first extracted with water or a dilute aqueous alkaline solution and then further extracted stepwise with aqueous alkaline solutions with gradually increased concentrations.

The primary object of this invention, therefore, is to provide a method for advantageously producing a nitrogen-containing polysaccharide having an excellent anti-tumour activity as well as other various pharmacodynamic effects from the fungus belonging to the Coriolus of the Basidiomycetes. The other objects of this invention will become apparent from a review of the following detailed description of the invention.

DETAILED DESCRIPTION OF THE INVENTION

The "fungus belonging to the Coriolus genus" used as starting material in this invention is a known species of the fungi belonging to Polyporaceae of the class Basidiomycetes, and such species includes, for example, *Coriolus versicolor* (Fr.) Quél., *Coriolus hirsutus* (Fr.) Quél., *Coriolus consors* (Berk.) Imaz., *Coriolus conchifer* (Schw.) Pat., *Coriolus pubescens* (Fr.) Quél., *Coriolus pargamenus* (Fr.) Pat. and *Coriolus biformis* (Klotz.) Pat. (See COLORED ILLUSTRATIONS OF FUNGI OF JAPAN by Rokuya Imazeki and Tsuguo Hongo, Vol. I, 1974, and Vol. II, 1975). Among these fungi, *Coriolus versicolor* (Fr.) Quél.; *Coriolus consors* (Berk.) Imaz.; *Coriolus hirsutus* (Fr.) Quél.; and *Coriolus pargamenus* (Fr.) Pat. were deposited on Dec. 25, 1973 under FERM-P No. 2414; on June 24, 1971, under FERM-P No. 988; on Sept. 6, 1974 under FERM-P No. 2711; and on Sept. 6, 1974 under FERM-P No. 2712, respectively, in Fermentation Research Institute, Agency of Industrial Science and Technology (Chiba-shi, Japan) which is a governmental organ designated by the Director-General of the Patent Office of Japan. The term "fungus belonging to the Coriolus genus" used herein is to be also understood as referring to the fruit bodies and/or mycelia of the above-mentioned species of fungi. Among them, most preferred for use in this invention are the mycelia obtained from artificial culture of *Coriolus versicolor* (Fr.) Quél.

This invention concerns a method of producing a nitrogen-containing polysaccharide by refining an extract of the fruit bodies and/or mycelia of the Basidiomycetes with an aqueous solvent, such method being characterized in that the extraction is first carried out with water or a dilute alkaline solution and then further practiced stepwise by using alkaline solutions with gradually increased concentrations.

For extracting the desired nitrogen-containing polysaccharide from the Basidiomycetes (starting material) according to the method of this invention, the starting material is subjected to plural extraction treatments (multiple-stage extraction), that is, the starting material is first extracted by using water or an aqueous solvent containing a small amount of alkali (a dilute alkaline solution) and then further extracted in multiple stages by using the aqueous solutions with the gradually increased alkali concentrations. In the course of this extraction process, it is possible to repeat extraction by using an extraction solution of a same concentration. The "aqueous solvent containing a small amount of alkali" means an aqueous solution in which, when mixed with the fungus, gives an aqueous phase of a pH around 7 or lower. Such specific definition is based on the fact that when pure water or a sodium hydroxide solution with concentration of around 0.01 N is mixed with the fungus, the pH of such solution remains within the range of around 4 to 7 due to the buffer action inherent to the fungus.

As for the aqueous alkaline solutions used at gradually increased concentrations in this invention, it is preferrable to adjust the concentrations of such solutions such that the maximum concentration is around 2 N or lower. This is because of the fact that decomposition of the active component could take place if extraction is carried out at a concentration higher than the above-mentioned level. The aqueous solvent employed for the extraction of the Basidiomycetes in this invention is used in an amount of 5 to 200 times by weight the starting material (based on dry weight) in each extraction stage, and usually such extraction is carried out at 50° to 100° C. for 20 minutes to 5 hours. It should be noted that an extraction temperature of lower than 50° C. results in poor extraction efficiency while an extraction temperature of over 100° C. could cause degeneration of the final product. The number of extraction stages is usually 2 to about 10, preferably 3 to about 8. It is preferable for preventing decomposition of the active component that the total heating time under the above-mentioned temperature is less than 20 hours irrespective of the number of extraction stages. It is also recommended that the total heating time is not less than 1 hour for attaining satisfactory extraction efficiency. The alkali used in this invention may be sodium hydroxide, potassium hydroxide, calcium hydroxide or ammonia, but use of sodium hydroxide is most general.

The above-described multiple-stage extraction method using the aqueous alkaline solutions with gradually increased concentrations provides a higher yield of the final product than attainable with the conventional methods and hence is of great significance from the viewpoint of industrial productivity. That is, such multiple-stage extraction process produces a surprisingly high yield as compared with repetitive extraction using pure water alone or an aqueous alkaline solutions of the same concentration.

The mechanism that produces such high extraction yields in the method of this invention is not yet definitely known, but it is considered that such extraction process not merely induces elution of the soluble components from the Basidiomycetes but also causes mild decomposition of the Basidiomycetes to produce the soluble active component. In other words, it is considered that the starting material undergoes decomposition each time the alkali concentration of the alkaline aqueous solution used in the extraction is elevated, allowing efficient generation of the active component.

On the other hand, if extraction is carried out by using a highly concentrated aqueous alkaline solution from the beginning without a preliminary water extraction, the extract yield is indeed relatively high in the first stage of the extraction but such yield drops sharply in the second and succeeding extractions. This is considered due to the fact that, the desired fraction that should normally be extracted with hot water or a dilute alkaline aqueous solution undergoes decomposition to an excessive degree under these conditions and, as a result, the object high molecular weight polysaccharide is reduced in a low molecular weight substance of a molecular weight of less than 5,000.

The extract obtained in the manner described above according to the method of this invention is neutralized according to an ordinary method by using a mineral acid such as dilute hydrochloric acid and then subjected to a refining process. In this case, the extract solution obtained on each extraction may be subjected to refining, or the solutions obtained in the respective stages of extraction may be combined together and then subjected to refining.

There are available various refining methods such as ultrafiltration, reverse osmosis, gel filtration, salting-out and precipitation by use of an organic solvent, which may be used either singly or in combination. Such refining of the extract solution can produce a preferred nitrogen-containing polysaccharide having an anti-tumour activity.

The elemental analysis of the thus obtained nitrogen-containing polysaccharide revealed that it is primarily composed of carbon, hydrogen, nitrogen and oxygen. The nitrogen content in the product varies depending on the nitrogen content in the starting material, but it was noticed that the product containing nitrogen of usually more than 2 weight%, in most cases 3 to 5 weight%.

Various color reaction tests on this substance gave the results such as shown in Table 1 below.

TABLE 1

| Color reaction | Color | Results |
| --- | --- | --- |
| α-naphthol sulfuric acid reaction (Molish's reaction) | Purple | Saccharides Confirmed |
| Indole sulfuric acid reaction (Disch's reaction) | Brown | Saccharides Confirmed |
| Anthrone sulfuric acid reaction | Greenish blue | Saccharides Confirmed |
| Phenol sulfuric acid reaction | Brown | Saccharides Confirmed |
| Tryptophane sulfuric acid reaction | Purplish brown | Saccharides Confirmed |
| Lowry-Foli process | Blue | Peptide bonds Confirmed |
| Ninhydrin reaction after hydrochloric acid hydrolysis | Purplish blue | α-amino acids Confirmed |

The results of these color reactions attest to the fact that the final product of this invention is a nitrogen-containing polysaccharide (containing primarily peptide-bonded nitrogen).

It was determined by column chromatography that the molecular weight of the present substance is within the range of approximately 5,000 to 300,000, and the average molecular weight, as measured by an ultra-centrifugal method, is within the range of 10,000 to 100,000. The low molecular weight fractions (with molecular weight of less than 5,000) discharged from the above-described refining treatment are almost nil in inhibitory effect against Sarcoma-180 solid tumours in mice upon intra-peritoneal administration, and also they have bitterness, disagreeable odor and induce side actions. Therefore, it is considered that these low molecular weight substances contribute nothing to the pharmacodynamic effect of the object nitrogen-containing polysaccharide of this invention but are rather detrimental to the desired effect.

The nitrogen-containing polysaccharide obtained according to the method of this invention shows anti-tumour activity in mice not only in intra-peritoneal administration but also in oral administration. In other words, this nitrogen-containing polysaccharide proves an excellent anti-tumour agent for oral administration, and in fact, such effect has been confirmed in various experiments such as mentioned in the following embodiments. Use of the nitrogen-containing polysaccharide is not limited to an oral anti-tumour agent; it also proves effective in aiding in the recovery of immunity by the host. Also, the nitrogen-containing polysaccharide of this invention produces an excellent effect, through oral administration, for improving the liver function, increasing appetite, remedying intestinal disorders and promoting urination. It also proves effective for treatment of leprosy.

EXAMPLE 1

200 gr of dry mycelia (moisture content: 9.9%) of Coriolus versicolor (Fr.) Quél. (FERM-P No. 2414) obtained from an artificial culture and 3 liters of water were put into a 5-liter-capacity flask equipped with an agitator, and the mixture was agitated in a boiling water bath and maintained under this condition at an internal temperature of 95°±2° C. for 3 hours. Then the mixture was cooled and subjected to suction filtration by using a Buchner funnel to separate the fungus and the extract solution, and then the residual mycelia were washed with about 1 liter of water which was mixed with the extract solution. The mixed solution was about 3.5 liters. pH of the extract solution was 5.8. The residual mycelia were further mixed with 2 liters of water, then subjected to a similar 2-hour extraction and washing with 1 liter of water to obtain about 3 liters of extract solution. The resultant fungus residue was again mixed with 2 liters of 0.1 N sodium hydroxide solution and similarly extracted at 95°±2° C. for 2 hours, followed by cooling, neutralization with 2 N hydrochloric acid and suction filtration to separate the extract solution and the fungus residue. After separation, the residue was washed with about 500 cc of water and mixed with the extract solution to obtain 2.5 liters of solution. Similar operations were repeated by using 2 liters of 0.2 N, 0.3 N and 0.4 N sodium hydroxide solutions and 0.5 liter of washing water, obtaining about 2.5 liters of extract solution from each process.

These six preparations of extract solutions (total 16.5 liters) were put together and concentrated by a vacuum concentrator (rotary evaporator) at 60° C. to 700 cc and then put into a dialytic cellulose tube (Visking Tube by Union Carbide Corp.) for current dialysis at 5° C. for 72 hours, and the obtained dialyzate was further concentrated and subjected to freeze-drying to obtain 60 gr of liver brown powder with moisture content of 7% (yield: 31.1%). The elemental analysis of this powder gave 40.3% carbon, 6.2% hydrogen, 2.9% nitrogen and 50.6% oxygen. The molecular weight of this substance, as measured according to column chromatography, was approximately 10,000 to 250,000, and the average molecular weight, as measured by an ultra-centrifugal method using water as solvent, was 94,000. (The oxygen content given above is the value obtained by subtracting the total percent of other elements from 100).

Various color reaction tests conducted on this powder after dissolving it in water gave the results same as shown in Table 1, and it was thus confirmed that this powdery substance is a nitrogen-containing polysaccharide. The inhibition ratio of this substance against Sarcoma-180 solid tumours in mice was as high as 90% in intra-peritoneal administration and 70% in oral administration.

The anti-tumour effect of this substance was measured according to an ordinary method which is briefly described below.

Sarcoma-180 tumour cells were transplanted in the abdominal cavities of mice and, after allowing sufficient growth for 7 days, $10^6$ of these cells were transplanted under the skin of the axilla of other mice to form solid tumours. Administration of the substance of this invention was started from 24th hour after transplantation. In the case of intra-peritoneal administration, the substance was administered in a dose of 10 mg/kg once every other day for 20 days for the total dosage of 0.2 ml/20 gr (mouse body weight), and in the oral administration, the substance was administered in a dose of 1,000 mg/kg once a day for 20 days for the total dosage of 0.2 ml/20 gr (mouse body weight). The tumours were enucleated on 25th day after transplantation, and the tumour growth inhibition ratio (%) was calculated from the average tumour weight in mice to which the substance of this invention was administered and the average tumour weight in control mice.

The results of similar extraction experiments carried out by using water alone as solvent are shown in Table 2 below. In these experiments, all of the extraction and washing steps were practiced by using water in the same amount as the solvent used in the above-mentioned treatments. In this case, the extract solution (mixed with washing water) was subjected to vacuum concentration, dialysis, cooling and drying to determine the yield in each run of extraction, and its result was shown in the table. As apparent from this table, the extraction yield drops sharply from 2nd and succeeding extractions, and it is hardly possible to obtain the object substance in a high yield from repetitive extractions.

TABLE 2

| Stage of extraction | Extract solution (l) | Washing solution (l) | Dry powder yield (wt %) |
| --- | --- | --- | --- |
| 1 | 3 | 1 | 7.0 |
| 2 | 2 | 0.5 | 2.1 |
| 3 | 2 | 0.5 | 0.8 |
| 4 | 2 | 0.5 | 0.3 |
| 5 | 2 | 0.5 | 0.1 |
| 6 | 2 | 0.5 | 0.1 |
| Total | 13 | 3.5 | 10.4 |

(Note):
Amount of mycelia used as starting material: 200 gr.
Extraction temperature: 95 ± 2° C.

EXAMPLE 2

By using the same apparatus as employed in Example 1, 200 gr of dry mycelia (moisture content: 8.8%) of *Coriolus versicolor* (Fr.) Quél. (FERM-P No. 2414) was extracted by using 2 liters of 0.5 N, 0.1 N, 0.2 N and 0.4 N sodium hydroxide solutions successively. The extraction temperature was 90° to 95° C. and extraction time was 2 hours in each extraction, and after each extraction the mixture was cooled, neutralized with 2 N hydrochloric acid solution and then subjected to suction filtration to separate the fungus residue and extract solution. The residue was washed with 500 cc of water after each extraction, and the washing solution was mixed with the corresponding extract solution.

The extract solution in each extraction was subjected to vacuum concentration, dialysis, concentration and freeze-drying in a similar way to Example 1 to obtain a liver brown powder.

The results of the experiments on the products in the respective extraction operations are shown in Table 3 below.

TABLE 3

| Stage of extraction | Sodium Hydroxide concentration | pH at the time of extraction | Dry powder yield (wt %) |
| --- | --- | --- | --- |
| 1 | 0.05N | 9.0 | 10.1 |
| 2 | 0.1N | 11.5 | 3.5 |
| 3 | 0.2N | 12.5 | 6.8 |
| 4 | 0.4N | 13.0 | 6.6 |

The total yield was 27%, and an elemental analysis of each product gave the following results: carbon, 41.0%; hydrogen, 6.3%; nitrogen, 3.7%; oxygen, 49.0%.

From the tests same as practiced in Example 1, it was confirmed that the above-mentioned powder is a nitrogen-containing polysaccharide having molecular weight of 10,000 to 250,000 and average molecular weight of 100,000. Inhibition ratio against Sarcoma-180 solid tumour in mice was 93% in the case of intra-peritoneal administration and 73% in the case of oral administration.

For sake of comparison of extraction yield, the same experiments as Example 1 were carried out by using 1 N and 0.4 N sodium hydroxide solutions to obtain the results shown in Table 4 below. As noted from the table, the yield has dropped as the extraction operation was repeated by using extraction solutions of the same concentration, and it was found quite difficult to obtain a high yield such as attained from multiple-stage extraction in the method of this invention.

TABLE 4

| Stage of extraction | Yield (wt %) of object material in extraction with 1N NaOH | Yield (wt %) of object material in extraction with 0.4N NaOH |
|---|---|---|
| 1 | 10.5 | 13.8 |
| 2 | 2.4 | 2.9 |
| 3 | 1.1 | 2.0 |
| 4 | 0.5 | 1.5 |
| Total | 14.5 | 20.2 |

EXAMPLE 3

By using the same apparatus as employed in Example 1, 200 gr of dry mycelia (moisture content: 9.9%) of Coriolus versicolor (Fr.) Quél. (FERM-P No. 2414) was first extracted with 3 liters of water at 95°±2° C. for 3 hours and then, after cooling, subjected to suction filtration to separate the residual mycelia and extract solution, and the residual mycelia were further washed with 1 liter of water and then mixed with the extract solution to obtain about 3.5 liters of extract solution.

Then the residual mycelia was placed in 2 liters of 1 N sodium hydroxide solution for extraction at 90° to 95° C. for 0.5 hour, which was followed by cooling, neutralization with 2 N hydrochloric acid, suction filtration and washing with 1 liter of water, thereby separating 3 liters of extract solution and fungus residue.

All of the extract solutions obtained were put together and subjected to vacuum concentration, dialysis, further concentration and freeze-drying after the manner of Example 1 to obtain 33 gr of liver brown powder with 7.0% moisture content (yield: 21.0%). The result of an elemental analysis of this powder revealed that it is composed of 41.7% of carbon, 6.4% of hydrogen, 3.9% of nitrogen and 48.0% of oxygen. It was also confirmed by tests the same as practiced in Example 1 that this substance is a nitrogen-containing polysaccharide with molecular weight of 10,000 to 300,000 and average molecular weight of 98,000.

The inhibition ratio of this substance against Sarcoma-180 solid tumours in mice was as high as 94% in intra-peritoneal administration and 68% in oral administration.

EXAMPLE 4

By using the apparatus of Example 1, 200 gr of dry fruit bodies of Coriolus versicolor (Fr.) Quél. (FERM-P No. 2414) with moisture content of 8.7% was first extracted with 2.4 liters of water at 95°±2° C. for 3 hours and the product, after cooling, was subjected to suction filtration to separate the residue and extract solution, and the residue were further washed with 500 cc of water and mixed with the extract solution to obtain about 2.5 liters of extract solution.

The residue was then mixed with 2 liters of 0.4 N sodium hydroxide solution and extracted at 90°±2° C. for 1 hour, followed by cooling, neutralization with 2 N hydrochloric acid, suction filtration and washing with 500 cc of water to separate 2.5 liters of extract solution and residue. A similar extraction operation was repeated with 2 liters of 1 N sodium hydroxide solution at 80°±2° C. for 1 hour to obtain 2.5 liters of extract solution.

All of the extract solutions were put together and subjected to vacuum concentration, dialysis, concentration and freeze-drying in the same way as Example 1 to obtain 43.4 gr of a liver brown powder with moisture content of 7.5% (yield: 22%). The result of an elemental analysis of this powder showed 42.3% carbon, 6.5% hydrogen, 2.2% nitrogen and 49.0% oxygen. It was also confirmed by the same tests as Example 1 that this substance is a nitrogen-containing polysaccharide with molecular weight of 10,000 to 300,000 and average molecular weight of 110,000.

The inhibition ratio of this substance against Sarcoma-180 solid tumours in mice was as high as 96% in intra-peritoneal administration and 75% in oral administration.

For sake of comparison of extraction yield, a similar extraction process was performed by using water alone as extraction solvent. The yield of the object substance was only 7.6%.

What is claimed is:

1. A method of providing a nitrogen-containing polysaccharide substantially free from units having a molecular weight below about 5000 which comprises extracting said nitrogen-containing polysaccharide from a fungus of the genus Coriolus of the family Polyporaceae of the class Basidomycetes at a temperature of 50° to 100° C. wherein:
    (a) a first extraction step is conducted with water or a dilute aqueous alkaline solution;
    (b) a second extraction step is conducted in an alkaline medium having a normality higher than said first extraction step and below about 2.0; and
    (c) a third extraction step is conducted at a normality higher than said second extraction step and below about 2.0.

2. A method of claim 1, wherein said fungus is Coriolus versicolor (Fr.) Quél.

3. A method of claim 1, wherein a fourth extraction step is provided at a normality higher than said third extraction step and at a normality below about 2.0.

4. A method of claim 1, wherein each alkaline phase includes sodium hydroxide.

* * * * *